United States Patent [19]
Schoeffler et al.

[11] Patent Number: 5,850,284
[45] Date of Patent: *Dec. 15, 1998

[54] APPARATUS FOR DETECTING A POLARIZATION ALTERING SUBSTANCE ON A SURFACE

[75] Inventors: Daniel Schoeffler, Huntington; Howard Stern, Greenlawn; Pat V. Costa, Nissequogue, all of N.Y.

[73] Assignee: Robotic Vision Systems, Inc., Hauppauge, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 487,249

[22] Filed: Jun. 13, 1995

[51] Int. Cl.$^6$ .............................. G01J 4/00; G08B 19/02
[52] U.S. Cl. ............................ 356/369; 340/583
[58] Field of Search ................... 356/364–370; 250/225, 341.8, 339.11, 339.12; 348/61; 340/583, 580, 581, 962, 602; 244/134 R, 134 F

[56] References Cited

U.S. PATENT DOCUMENTS

| | | | |
|---|---|---|---|
| 3,633,212 | 1/1972 | Cooper | 356/369 |
| 5,243,185 | 9/1993 | Blackwood | 250/225 |
| 5,475,370 | 12/1995 | Stern | 356/369 |
| 5,500,530 | 3/1996 | Gregoris | 250/339.11 |
| 5,532,738 | 7/1996 | Stern | 356/369 |
| 5,557,261 | 9/1996 | Barbour | 340/580 |
| 5,589,822 | 12/1996 | Stern | 356/369 |
| 5,617,076 | 4/1997 | Stern | 356/369 |
| 5,650,610 | 7/1997 | Gagnon | 356/369 |

*Primary Examiner*—Hoa Q. Pham
*Attorney, Agent, or Firm*—Morrison Law Firm

[57] ABSTRACT

An apparatus for detecting a polarization altering substance, such as ice, on a surface includes a polarizing filter on the surface between the surface and the polarization altering substance. When the polarizing filter includes alternating regions having orthogonal polarizing properties, only one viewing of the surface through a blocking filter is required. When light, either polarized or unpolarized, reflects off the surface, it passes through the polarizing filter and becomes polarized. Reflected light that additionally passes through ice after leaving the polarizer becomes unpolarized. When viewed through a blocking polarizer filter, polarized light passing through ice appears bright due to the unpolarizing effect of ice. On the other hand, polarized light not passing through ice retains its polarization and appears dark when viewed through a blocking filter. Since the polarizing filter is between the surface and the viewer, the surface can be metallic, dielectric, or painted without affecting the results. If the proper blocking orientation for the viewer is not known in advance, the Stokes coefficients can be calculated if views are taken through a series of specified polarizing filters. The ratio of polarized light returned to the viewer compared to the unpolarized light returned to the viewer can then be calculated from any arbitrary position. A retroreflective substance on the surface further enhances the effect for systems employing an active illumination source located coaxially with or adjacent to the imaging system.

22 Claims, 7 Drawing Sheets

APPARATUS FOR DETECTING A POLARIZATION ALTERING SUBSTANCE ON A SURFACE

BACKGROUND OF THE INVENTION

This invention relates to using a polarizer on a surface for detecting the presence of a polarization altering or opaque substance on the surface. In particular, this invention relates to detecting ice on a surface using a polarizer on the surface, and especially when the surface is an aircraft wing or other aircraft exterior or control surface. This invention also relates to detecting ice on a road or roadside surface.

Current airport aviation practices depend on the use of de-icing fluid to remove ice and prevent its future build-up for time periods of 5–30 minutes. Verification that wing and other aerodynamic or control surfaces are free of ice is done visually, often under difficult viewing conditions such as bad weather or darkness. Occasionally, significant ice build-ups are not noticed, sometimes leading to tragic results. Clear ice, sometimes called black ice, is particularly difficult to see since it is transparent and does not give an optical contrast between iced and non-iced surfaces. Even though virtually invisible under certain circumstances, clear ice nevertheless corrupts the aerodynamic surfaces of an aircraft, and adds a weight burden.

The aircraft crew has primary responsibility for detecting such ice. Reliance is on visual viewing supplemented with an ordinary flashlight if necessary. A need exists for a system which is capable of accurately and easily determining the presence of ice on an aircraft wing. The present invention seeks to use the properties of polarized light for the development of such a system.

In the wave theory of light, light radiation is thought of as a system of transverse waves or undulations. Transverse waves are waves that undulate at right angles to the direction the waves move. For example, ocean waves undulate up and down as the waves move towards the shore. Unpolarized light undulates, or oscillates, in all directions equally. Planar, or linear, polarized light oscillates in one plane only. Plane polarization is similar to the action produced by flipping a rope which has one end tied to a wall. As the rope is given an up and down motion, a traveling wave is propagated down the rope to the wall. In like manner, a sideways motion of the rope induces a horizontal wave. These wave motions, each in a single plane, are analogous to the single plane oscillations of polarized light. A linear polarizer changes unpolarized light to polarized light, usually by permitting only linearly polarized light to pass through and absorbing or reflecting the remainder.

Light can also be circularly polarized. Using the rope analogy, if at the same time that the rope is flipped up and down, the rope is also given a rotary motion, the induced wave travels down the rope in a helical fashion. This helical motion is analogous to circularly polarized light. Circularly polarized light is polarized light whose oscillations do not remain constantly in one direction. Instead, the oscillations successively take on different directions for each wavelength uniformly through a rotation of 360°. Circularly polarized light is categorized as being either righthanded (clockwise looking towards the source) or lefthanded (counterclockwise looking toward the source).

An optical isolator is a circular polarizer that is usually implemented from a linear polarizer and a quarter wave retarder plate that has its fast and slow axes located 45 degrees from the polarization axis of the linear polarizer. Unpolarized light first passing through the linear polarizer and then the retarder becomes circularly polarized. The "handedness" of the circular polarizer depends on the relationship between the fast axis of the retarder plate and the axis of the polarizer (plus or minus 45°).

Metallic surfaces, as well as surfaces painted with metallic paint reflect polarized light differently than dielectric surfaces. Metals and metallic paints reverse the rotational direction of circularly polarized light. For example, specular reflection (the reflection from a perfectly smooth surface without any diffusion effects) of clockwise circularly polarized light from a metal surface is counterclockwise circularly polarized and vice versa. This effect is used in the construction of optical isolators which permit light initially to pass through the isolator and prevent specularly reflected light from returning through the isolator back to the source.

When a metallic surface (or surface painted with a metallic paint) is illuminated with circularly polarized light and the reflected energy viewed through the same circular polarizer, the resulting image is extremely dim since the circular polarizer acts as an isolator with respect to the specular reflection from the metal surface. Other types of surfaces (birefringent, certain dielectric, matte, etc.) viewed through the same circular polarizer maintain their normal brightness because the circular polarization is destroyed upon reflection. If the circular polarizer is flipped (reversed) so that the quarter wave retarder precedes the linear polarizer, the combination no longer acts as an isolator for the illuminating beam. The metallic surface's reflected image is then of normal (bright) intensity.

Most non-metallic and painted or matte surfaces illuminated with circularly polarized light and viewed through the same circular polarizer maintain their normal apparent intensity. Such surfaces, including ice on the metal, whether matte white due to a snow covering or crystal clear due to even freezing, destroys the circular polarization of the reflected light and therefore produces the same depolarizing property as a matte painted surface with respect to the optical isolator. A transparent dielectric over metal depolarizes circularly polarized light passing through it if it has numerous internal point scatterers or is birefringent. Birefringence is the ability of some transparent solids to bend, or delay, light rays by two slightly different amounts depending on the polarization. Birefringence occurs because the orderly array of atoms in a crystalline lattice creates an asymmetry, known as anisotropy, in the properties of the material. Ice has this characteristic. Thus, circularly polarized light reflected from a painted surface, snow, ice, or even transparent ice over metal is depolarized and is not affected by the isolator.

Therefore, the image of a clear metal surface that is ice free alternates between dark and bright when alternately viewed through an isolator and non-isolator structure, respectively. Apparatus other than the combination of optical isolators and non-isolators can produce the same effect. A combination of crossed and uncrossed linear polarizers in the illumination and viewing path produces the same effect. Any ice or snow covering the metal surface causes the image to maintain approximately the same brightness regardless of whether it is viewed through an isolator or non-isolator structure or equivalent structures.

Since the reflected light from a specular surface is highly directional, changes in the illumination angle should be minimized when changing from isolator to non-isolator state. Otherwise, a change in reflected light intensity caused by a change in illumination angle may be erroneously interpreted as being caused by the isolator/non-isolator effect. The equipment used needs to accommodate a large dynamic range of received light intensities due to the high directionality of specular reflection. Saturation due to high light levels within the receiver can cause erroneous results if not properly handled.

Compensation must be made for background light, such as sunlight, or the system is limited to operation in low light levels. Light reflected from surfaces other than the aircraft wing when viewing downward on the wing, such as the ground, must also be removed in order to provide an unmistakable image of the wing or any patches of ice on it.

Specular surfaces viewed at right angles (normal) to the surface provide a relatively high isolator/non-isolator ratio and therefore a clear demarcation between the two light levels. However, as the surface is viewed at angles away from normal to the surface, which is necessary with a system viewing from a fixed location, the isolator/non-isolator ratio decreases. The reflected light becomes similar to that produced by reflection from a contaminated surface, such as snow or through ice, thereby making it more difficult to distinguish between the contaminated surface and the uncontaminated surface viewed at a large angle with respect to its normal.

As outlined above, the use of polarized light according to the prior art to detect ice is subject to various limitations. Prior art methods for determining the presence of ice on a surface depend on shining polarized light onto the surface. Some methods are not effective for detecting the presence of ice on a surface in sunlight or strong artificial light. Detecting the presence of ice on a surface is limited by a viewing angle of a camera or other optic device. In addition, prior art methods using polarization do not detect the presence of ice on non-metallic surfaces or surfaces painted with non-metallic paint. Finally, prior art methods require comparing two images; one using a blocking filter and one using an non-blocking filter.

OBJECTS AND SUMMARY OF THE INVENTION

Accordingly, an object of the present invention is to provide a method for detecting ice on a surface that overcomes the drawbacks and limitations of the prior art.

Another object of the present invention is to provide a method for determining the presence of ice on a surface that does not depend on shining polarized light onto the surface.

It is a further object of the present invention to provide a method for detecting the presence of ice on a surface that is effective using either ambient or artificial light.

It is a still further object of the present invention to provide a method for detecting the presence of ice on a surface that is relatively insensitive to a viewing angle of a camera or other optical device.

It is a still further object of the present invention to provide a method for detecting the presence of ice on a non-metallic surface or on a surface painted with a non-metallic paint.

It is a still further object of the present invention to provide a method for detecting the presence of ice on a surface which requires taking only one image of that portion of the surface that is to be inspected.

Briefly stated, an apparatus for detecting a polarization altering substance, such as ice, on a surface includes a polarizing filter on the surface between the surface and the polarization altering substance. When the polarizing filter includes alternating regions having orthogonal polarizing properties, only one viewing of the surface through a blocking filter is required. When light, either polarized or unpolarized, reflects off the surface, it passes through the polarizing filter and becomes polarized. Reflected light that additionally passes through ice after leaving the polarizer becomes unpolarized. When viewed through a blocking polarizer filter, polarized light passing through ice appears bright due to the unpolarizing effect of ice. On the other hand, polarized light not passing through ice retains its polarization and appears dark when viewed through a blocking filter. Since the polarizing filter is between the surface and the viewer, the surface can be metallic, dielectric, or painted without affecting the results. If the proper blocking orientation for the viewer is not known in advance, the Stokes coefficients can be calculated if views are taken through a series of specified polarizing filters. The ratio of polarized light returned to the viewer compared to the unpolarized light returned to the viewer can then be calculated from any arbitrary position. A retroreflective substance on the surface further enhances the effect for systems employing an active illumination source located coaxially with or adjacent to the imaging system.

According to an embodiment of the invention, an apparatus for detecting a polarization altering substance on a surface includes a first polarizing filter on the surface, the first polarizing filter including alternating regions having different axes of polarization, and means for viewing the surface through a second polarizing filter.

According to an embodiment of the invention, an apparatus for detecting a polarization altering substance on a surface includes a first polarizing filter on the surface, first means for viewing the surface through a second polarizing filter, the second polarizing filter being a blocking filter, second means for viewing the surface through a third polarizing filter, the third polarizing filter being an non-blocking filter, and means for comparing a response to the first means for viewing and the second means for viewing to determine a presence of the polarization altering substance.

According to an embodiment of the invention, an apparatus for detecting a polarization altering substance on a surface includes a filter on the surface, the filter including an unpolarized portion and two linear polarized portions, the two linear polarized portions having polarization axes 45 degrees apart, and means for viewing the surface through a linear polarized filter.

According to an embodiment of the invention, an apparatus for detecting a polarization altering substance on a surface includes a filter on the surface, the filter including at least one unpolarized portion and at least one polarized portion, means for providing a brightness reference in the at least one unpolarized portion, and means for viewing the surface through an aligned blocking polarized filter.

According to an embodiment of the invention, an apparatus for detecting a polarization altering substance on a surface includes a first polarizing filter on the surface, a filter strip including a series of specified filters, means for measuring a series of views through the filter strip, one view through each specified filter, to obtain a series of measurements, means for determining a set of Stokes coefficients from the series of measurements, and means for determining, from the set of Stokes coefficients, a ratio of polarized light returned from the surface compared to unpolarized light returned from the surface.

According to an embodiment of the invention, an apparatus for detecting a polarization altering substance on a surface includes a polarizing filter on said surface, means for determining at least two Stokes parameters, and means for measuring, from said set of Stokes parameters, a ratio of polarized light returned from said surface compared to unpolarized light returned from said surface.

According to an embodiment of the invention, an apparatus for detecting a polarization altering substance includes a retroreflective substance on a surface, a first polarizing filter on the retroreflective substance, the first polarizing filter including alternating regions having orthogonal polarizing properties, and means for viewing the retroreflective substance through a second polarizing filter effective for determining a presence of the polarization altering substance.

According to an embodiment of the invention, an apparatus for detecting a polarization altering substance on a surface includes a retroreflective substance on the surface, a first polarizing filter on the retroreflective substance, first means for viewing the retroreflective substance through a second polarizing filter, the second polarizing filter being a blocking filter, second means for viewing the retroreflective substance through a third polarizing filter, the third polarizing filter being an non-blocking filter, and means for comparing a response to the first means for viewing and the second means for viewing to determine a presence of the polarization altering substance.

According to an embodiment of the invention, an apparatus for detecting a polarization altering substance on a surface includes a retroreflective substance on the surface, a first polarizing filter on the retroreflective substance, a filter strip including a series of specified filters, means for measuring a series of views of the retroreflective substance through the filter strip, one view through each specified filter, to obtain a series of measurements, means for determining a set of Stokes coefficients from the series of measurements, and means for determining, from the set of Stokes coefficients, a ratio of polarized light returned from the retroreflective substance compared to unpolarized light returned from the retroreflective substance.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1:
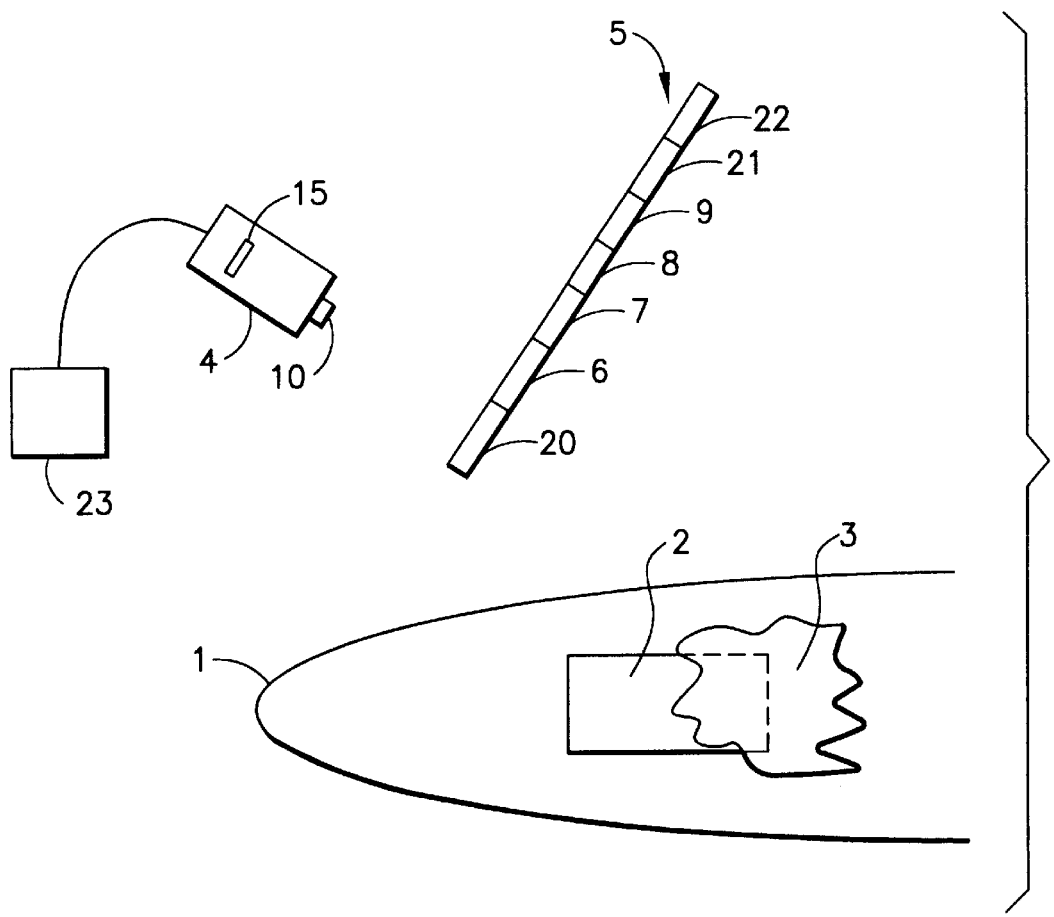
FIG. 1 shows an embodiment of the invention using either a linearly or circularly polarized filter patch on a surface of an aircraft wing.

Referring to FIG. 1, an embodiment is shown using either linear or circular polarizers placed on a surface, such as an aircraft wing 1. A linear polarized filter patch 2 is affixed to aircraft wing 1. An ice patch 3 partially covers filter patch 2. A video camera 4 observes the scene through one of a 0° polarizing filter 6, a 90° polarizing filter 7, a 45° polarizing filter 8, a 135° polarizing filter 9, an unpolarized filter 20, a CW polarized filter 21, and a CCW polarized filter 22, an angles being with respect to the direction of the linear polarization of filter patch 2. "CW" refers to clockwise circular polarization and "CCW" refers to counterclockwise circular polarization. All filters 6–9 and 20–22 are mounted to a filter strip 5 which is located between the scene and a camera lens 10 or between camera lens 10 and a video pickup device 15. The filters shown form a complete set that can be used to analyze a mixture of polarized and unpolarized light emanating from any point in the scene via computation of the well known Stokes parameters using the intensity observed at that point for each filter. Full analysis using the Stokes parameters is necessary only if the direction of polarization of filter patch 2 with respect to filter strip 5 is unknown. Further, if it is known a priori that the patches are linearly polarized, it is not necessary to use circular polarized filters for viewing. Conversely, if it is known that the patches are circularly polarized, it is not necessary to use linear polarized filters for viewing.

When the position of a viewing apparatus, such as video camera 4, varies greatly with respect to filter patch 2, isolating and non-isolating modes cannot be set up a priori since the proper filter orientation is not known in advance. One way of solving this problem is by taking an image using each of the filters 6–9 and 20–22 mounted to filter strip 5. Each image is sent to a computer 23 via a conventional frame snatcher (not shown), for analysis. The commercially available Cognex 4400, for example, combines frame snatching and computer functions.

Stokes coefficients, based on the well known Stokes parameters, are calculated at each point in the resulting images. The four Stokes parameters, I, Q, U, and V, give a complete description of polarized light. "I" is the total intensity, "Q" and "U" are two linear polarization components separated by 45°, and "V" is a circular polarization component. The Stokes coefficients are determined as follows.

$S_0$: The total energy observed through unpolarized filter 20.

$S_1$: The difference between the observed energy through 0° polarizing filter 6 and 90° polarizing filter 7.

$S_2$: The difference between the observed energy through 45° polarizing filter 8 and 135° polarizing filter 9.

$S_3$: The difference between the observed energy through CW polarized filter 21 and CCW polarized filter 22. The Stokes coefficients are not independent and can be determined with fewer measurements than described above.

The degree of polarization is computed as the square root of the sum of the squares of coefficients $S_1$, $S_2$, and $S_3$ divided by $S_0$.

Thus, the ratio of the polarized light returned (corresponding to the previous case of the isolating mode) to the non-polarized light returned (corresponding to the previous case of the non-isolating mode) can be found from any arbitrary position. It is known to those skilled in the art that different polarizing angles can be used along with a suitable modification of the equation for calculating the degree of polarization.

It is also known in the art that many schemes are available for rotating individual retarders or polarizers in a series combination of such devices to achieve the same end. Such schemes include using a rotating retarder plate, using a rotating polarizer, and using time varying retarder elements. Examples of the latter include the Zurich Imaging Stokes Polarimeters I and II (ZIMPOL I and II) as described in the article "Zurich Imaging Stokes Polarimeters I and II," SPIE Proceedings 2265, p. 222, 1994.

Figure 9:
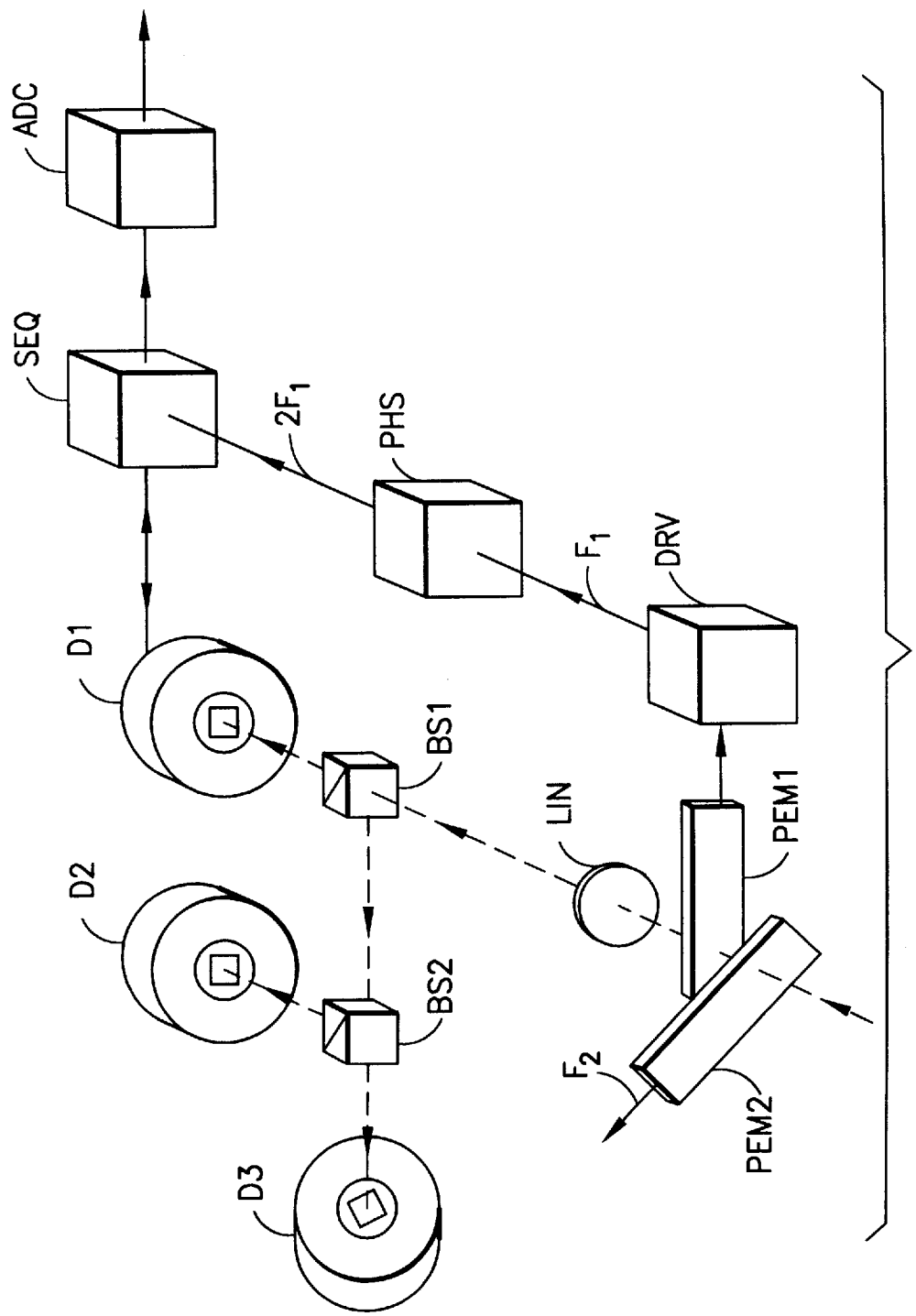
FIG. 9 shows a Zurich Imaging Stokes Polarimeter I used with an embodiment of the present invention.

Referring to FIG. 9, a photoelastic modulator based polarimeter for obtaining Stokes parameters using charge coupled devices (CCD's) is shown. This apparatus, the ZIMPOL I, was developed by Dr. Hanspeter Povel and Dr. Christoph Keller of the Swiss Federal Institute of Technology in Zurich, Switzerland. Each pixel in an image contains complete polarization information in the form of Stokes parameters.

A photoelastic modulator (PEM) is a variable retarder with a fixed fast axis and sinusoidally varying retardation based on stress-induced birefringence. A PEM is usually a bar or rod of any highest quality optical glass which normally has no polarizing properties. A standing acoustic wave at the fundamental mode frequency is set up in the PEM by a piezoelectric transducer. The acoustic vibration induces an oscillating birefringence proportional to the strain produced by the fundamental mode vibration. Since the vibration is sinusoidal, a retardation $\delta_m$ also varies sinusoidally according to the equation $$\delta_m = A\sin\omega t,$$

where $\omega$ is the modulation frequency and A is the retardation amplitude.

Two photoelastic modulators, PEM1 and PEM2, have frequencies $f_1$ and $f_2$, respectively. Photoelastic modulators PEM1 and PEM2 have their modulator axes oriented 45° to each other. A lightbeam L passes through photoelastic modulators PEM1 and PEM2 before passing through an achromatic linear polarizer LIN. A passing axis of linear polarizer LIN bisects the modulator axes of photoelastic modulators PEM1 and PEM2. Lightbeam L with Stokes vector (I, Q, U, V) constant in time entering PEM1 produces the following intensity variations after leaving linear polarizer LIN:

$$I'(t) = \tfrac{1}{2}(I + Q\sqrt{2}J_2(A)\cos(2\Omega_1 t) + U\sqrt{2}J_2(A)\cos(2\Omega_2 t) + V\sqrt{2}J_1(A)\sin(\Omega_1 t)).$$

$\Omega_1$ and $\Omega_2$ are the oscillation frequencies of PEM1 and PEM2. $J_1$ and $J_2$ are the Bessel functions of order 1 and 2. The amplitude of both PEM,s, A, is chosen such that $J_0(A)=0$. Thus, lightbeam L is proportional to Q at frequency $2\Omega_1$, to U at $2\Omega_2$, and to V at $\Omega_1$. Measuring lightbeam L at these frequencies allows the Stokes parameters to be determined.

A first beamsplitter BS1 divides lightbeam L to a first CCD D1 and a second beamsplitter BS2. Second beamsplitter BS2 further divides lightbeam L to second and third CCD's D2 and D3. First, second, and third CCD's D1, D2, and D3 detect $\Omega_1$, $2\Omega_1$, and $2\Omega_2$.

A driver DRV receives frequency $f_1$ from a driver electronics portion of PEM1. Driver DRV sends this sinusoidal reference signal to a phase shifter PHS which produces an output and doubles the frequency to $2f_1$. Phase shifter PHS adjusts for the phase shift between the optical modulation and the electronic demodulation. CCD control electronics (not shown) uses the output from phase shifter PHS during a synchronous integration phase. CCD D1 is read out by a sequencer SEQ at a rate of 3.3 Mpixels per second via correlated double sampling digitized to 12 bits by analog/digital converter ADC. CCD's D2 and D3 are read out in a similar manner.

Each CCD is a "slow" optical detector array, with, for example, a 50 Hz frame rate. Each CCD is used as a detector and demodulator for the PEM modulation signals, which are typically around 42 KHz. Each CCD detector includes a mask that covers every other row of pixels. Each covered pixel is paired with an open pixel. Charge accumulates in the open pixel proportional to a number of photons which strike it. The charge on the pixels is switched between the open and covered pixels by an appropriate square-wave reference signal. Both charge images accumulate for a period of time, typically less than one second, before the CCD array is read out. The ZIMPOL I records simultaneously the intensity I and one of the polarization parameters, Q, U, or V.

Another apparatus, the ZIMPOL II (not shown), uses a single CCD with a micro-lens array which collects all the incident light on the CCD array. Two photoelastic modulators are synchronized at a same frequency with a 90° phase difference. Modulator axes of the two photoelastic modulators are 45° apart. A lightbeam is focused on the CCD with the micro-lens array so that only one of four pixels in a column is used for light detection. The remaining three pixels are used for temporary charge storage. Four charge packets, one from each pixel, correspond to four independent linear combinations of the four Stokes parameters. These charge packets are sequentially shifted between the pixel rows in phase with a modulator reference signal. The four Stokes parameters are calculated from the digitized pixel charges after the CCD is read out.

Figure 10:
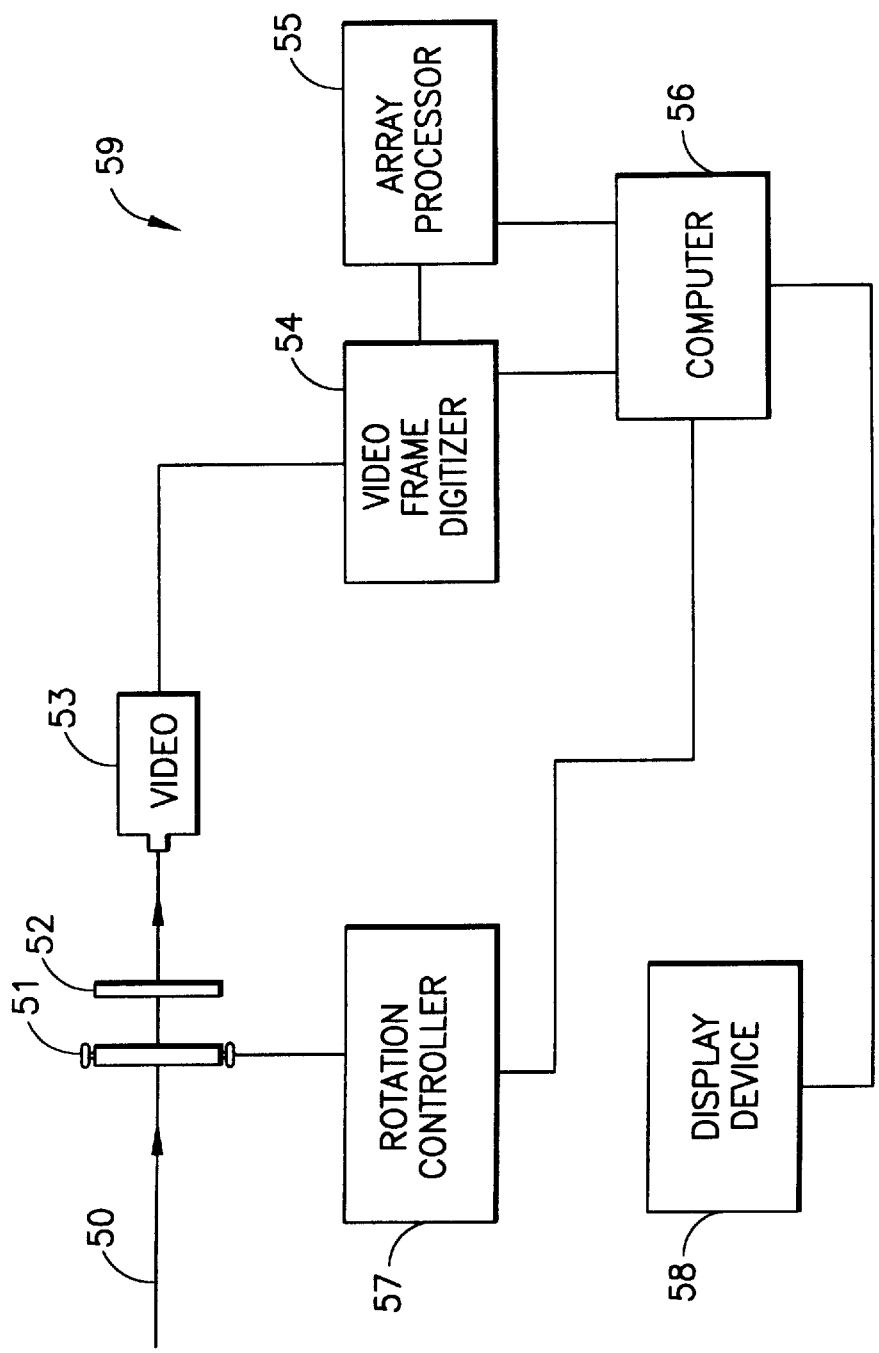
FIG. 10 shows an Imaging Stokes Polarimeter used with an embodiment of the present invention.

Referring to FIG. 10, one type of imaging Stokes polarimeter 59 is shown. Polarimeter 59 uses a rotating retarder to determine $S_0$, $S_1$, and $S_2$ from the equation $$I(\phi) = \tfrac{1}{2}(s_0 + \tfrac{1}{2}s_1(1+\cos(4\phi)) + \tfrac{1}{2}s_2\sin(4\phi) - s_3\sin(2\phi)).$$

If circular polarization is not present, $S_3$ equals zero. Taking measurements at zero degrees, 22.5 degrees, and 45 degrees allows a simultaneous solution for the coefficients since a minimum of three measurements are required to determine $S_0$, $S_1$, and $S_2$. $S_3$ can also be determined given a minimum of four measurements. Input light 50 is sinusoidally modulated by a quarter wavelength (¼λ) rotating retarder 51. Rotating retarder 51 is controlled by a rotation controller 57. The sinusoidally modulated light then passes through a fixed linear polarizer 52 to a video camera 53 where an image is recorded. The image is digitized by a video frame digitizer 54 and sent to an array processor 55. A computer 56 controls rotation controller 57, video frame digitizer 54, and array processor 55. Computer 56 processes the received information and sends it to a conventional display device 58 for display.

Figure 2A:
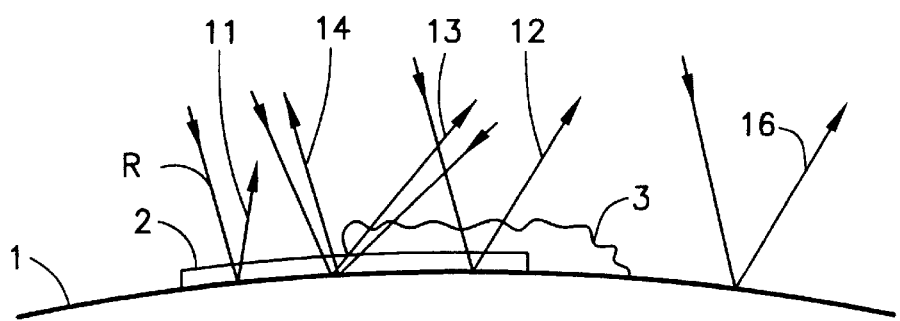
FIG. 2a shows a plurality of light rays reflected from a polarized filter patch.

Referring to FIG. 2a, a plurality of ambient light rays R pass through filter patch 2 affixed to aircraft wing 1 and are reflected toward camera lens 10. These rays R have different characteristics depending on whether and when they pass through ice patch 3. A reflected ray 11 avoids ice patch 3, and thus returns with a polarization dependent only on filter patch 2 on the surface of aircraft wing 1. A reflected ray 12 passes through ice patch 3 on the way in to the polarizer and on the way out. A reflected ray 13 passes through ice patch 3 only on the way out from the polarizer. A reflected ray 14 passes through ice patch 3 only on the way in to the polarizer. A reflected ray 16 is reflected by the aircraft surface or by an opaque coating (not shown), such as snow, on filter patch 2. The ratio of unblocked to blocked light is properly high for ray 11 (no ice) and is lower due to depolarization for rays 12 (ice), 13 (ice), and also 16 since ambient light is primarily unpolarized. Ray 14 gives a false reading since the light is not depolarized by the ice on the way out. However, ray 14 is a rare case, occurring only in the transition region at an edge of an ice/noice interface, so that its effect can be ignored.

Figure 2B:
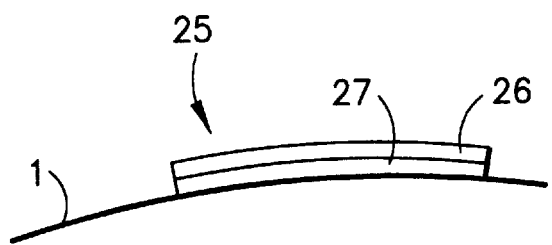
FIG. 2b shows a circularly polarized filter patch on a surface of an aircraft wing.

Referring to FIG. 2b, a circular polarizing filter patch 25 includes a quarter wave retarder material 26 and a linear polarizing material 27 that must be placed in the order shown. That is, material 27 is affixed on aircraft wing 1, while material 26 is between material 27 and camera lens 10. An axis of linear polarizing material 27 must be at an angle of 45° to a fast axis of retarder material 26 to create the desired circular polarizing effect. Equivalent results are obtained from viewing filter patch 25 with a circularly polarized blocking filter (not shown) and a circularly polarized non-blocking filter (not shown) as are obtained viewing filter patch 2 with blocking filter 7 and non-blocking filter 6 as described above.

Figure 3A:
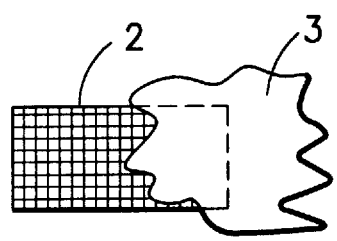
FIG. 3a shows an image obtained from viewing a polarized filter patch using a blocking filter.
Figure 3B:
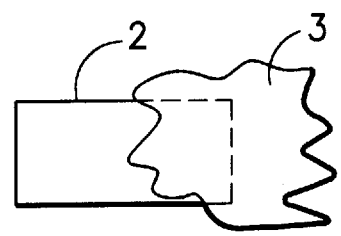
FIG. 3b shows an image obtained from viewing a polarized filter patch using an non-blocking filter.

Referring to FIG. 3a, an image is shown that results when video is obtained using filter 7 (blocking mode). Ice patch 3 covers part of filter patch 2. FIG. 3b shows the result obtained using filter 6 (non-blocking). Both images are taken from the same advantageous location. The ice-free surface appears very dark in the blocking mode image taken using filter 7 but not in the non-blocking mode image using filter 6. Ice patch 3 covering filter patch 2 appears much lighter than the ice-free surface in the blocking mode image due to the partial depolarization of the emerging (reflected) light by the ice.

Blocking and non-blocking images can be obtained by a person looking through a pair of polarized glasses (not shown). If the two lenses are orthogonally polarized with respect to each other, for example, if the left lens is horizontally polarized and the right lens is vertically polarized, and the person viewed filter patch 2 at a polarization angle of exactly 45 degrees, the person would see the same amount of light through each eye. Assuming no ice is present on filter patch 2, slowly rotating the head causes the image seen through one lens to slowly darken and the image seen through the other to become brighter. The presence of ice would cause the reflected light to appear more uniform while moving the head. Calculating the ratio of polarized light returned to the non-polarized light returned as described above using Stokes parameters or coefficients avoids the subjectivity involved when using human observation.

Figure 4A:
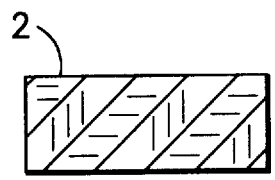
FIG. 4a shows a linear polarizing filter patch with alternating regions having orthogonal polarizing properties.
Figure 4B:
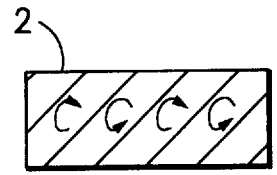
FIG. 4b shows a circularly polarizing filter patch with alternating regions having orthogonal polarizing properties.

Referring to FIG. 4a, an embodiment of filter patch 2 includes alternating diagonal stripes having orthogonal polarizing properties, such as, for example, 0° and 90° linear polarizing filter materials. Referring to FIG. 4b, an embodiment of filter patch 2 is shown which includes diagonal stripes of CW and CCW circular polarizing materials. For purposes of this discussion, CW and CCW circular polarizing materials are also characterized as orthogonal.

Figure 5A:
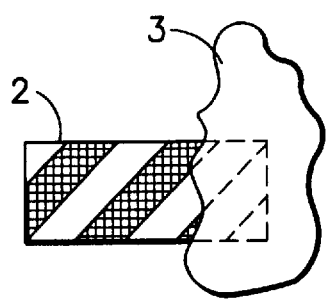
FIG. 5a shows an image obtained from viewing the linear polarizing filter patch of FIG. 4a through a linearly polarized filter.
Figure 5B:
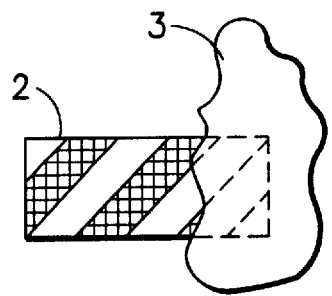
FIG. 5b shows an image obtained from viewing the circularly polarizing filter patch of FIG. 4b through a circularly polarized filter.

Referring to FIGS. 5a and 5b, results are shown from images taken in the blocking mode (using filter 7) and non-blocking mode (using filter 6) when filter patch 2 is made of alternating diagonal stripes having orthogonal polarizing properties as shown in FIGS. 4a and 4b, respectively. The stripes having orthogonal polarizing properties provide the necessary reference to allow computing an accurate ratio of the isolating (blocking) to non-isolating (non-blocking) properties within one image. Computing accurate ratios of the blocking to non-blocking properties allows accurate computation of the amount of depolarization due to the presence of ice or snow.

Although FIGS. 5a–5b show the results of both blocking and non-blocking mode images, it is readily apparent that either one of the two images satisfies the ice detection criteria since in either case half of the stripes are blocked. In both images, the contrast between the alternating stripes having orthogonal properties is very high within ice-free regions and much lower in regions that are covered by ice or snow. In other words, any polarizing filter is suitable for viewing the surface, although a linear polarized filter used for viewing should preferably have its axis aligned with that of one set of alternating stripes.

In an alternative embodiment (not shown), stripes include an alternating sequence of linear polarized stripes, all having their axes aligned, and stripes made of unpolarized material having approximately the same transparency as the linear polarized stripes. In this case, the unpolarized stripes provide a reference level for the brightness expected from the polarized stripes in the blocking image when ice completely depolarizes the received light. Since the unpolarized stripes have constant brightness for either blocking or non-blocking states, only the polarizing stripes serve as ice detecting surfaces.

Orienting a polarizing filter so that it is "blocking" or "non-blocking" is not necessary. It is only necessary to use a linear polarizing filter for viewing if the diagonal stripes include linearly polarized materials. If the diagonal stripes contain orthogonal circularly polarized materials, the viewing must be done through a circularly polarized filter. In either case, only one view or image need be obtained to detect the presence of ice on the surface.

Figure 6A:
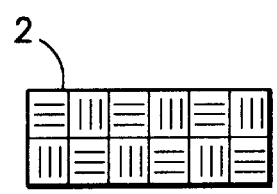
FIG. 6a shows an embodiment of a linear polarizing filter patch with alternating regions having orthogonal polarizing properties.
Figure 6B:
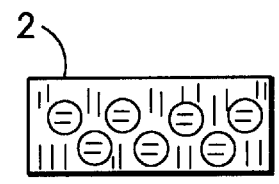
FIG. 6b shows an embodiment of a linear polarizing filter patch with alternating regions having orthogonal polarizing properties.

Of course, stripes are not the only pattern that may be used to partition the orthogonal polarizers. For example, a checkerboard pattern may be used or a pattern of circles on a solid background as shown in FIGS. 6a and 6b, respectively. It is only important that the pattern be easily differentiable into separate regions by either automated equipment that interprets the video or by an eye of a human operator looking through a polarizer.

When subdividing filter patch 2 into smaller subsections having orthogonal properties, it is desirable to paint the underlying surface to provide a matte or diffusing surface rather than a specular surface. The matte paint is useful because adjacent portions in the pattern may lie on a curved wing surface. If the surface is specular, adjacent portions may appear to have a different brightness solely because the normal to the local wing surface bisects the angle formed by the illumination source (the sun or floodlights, etc.), the illuminated point, and the viewing apparatus. A near-specular relationship increases the apparent brightness and one far from being specular decreases the apparent brightness. These variations in brightness, since they are not related to the polarization (or lack thereof) of the light, introduce an error into the computations of brightness ratios between the same region in different images or between adjacent regions (for the diagonal stripes or checkerboard, etc.) in the same image.

Figure 11A:
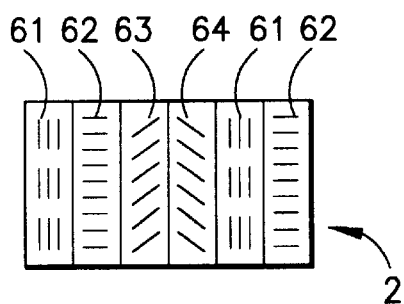
FIG. 11a shows an alternative embodiment of a polarizing filter patch.

Referring to FIG. 11a, an alternative embodiment for a polarizing filter patch 2 is shown. Filter patch 2 is subdivided into linearly polarized subsections 61, 62, 63, and 64 having polarizing axes aligned at zero degrees, 45 degrees, 90 degrees, and 135 degrees, respectively. Such a construction allows a complete determination of the amount of polarization, and hence any depolarization in ice covered regions, when viewed through a single linear polarizer at any orientation. Although the angle of the viewing polarizer is unknown, the four linearly polarized subsections 61, 62, 63, and 64, assuming an equal brightness of the surface under them, immediately provide the differences required to solve for the equivalent of the $S_1$ and $S_2$ coefficients as the difference in observed brightness between the zero and 90 degree subsections, and the difference in observed brightness between the 45 and 135 degree subsections, respectively. $S_1$ and $S_2$ must be compared to the sum of the light intensity coming from either the zero and 90 degree subsections or the 45 and 135 degree subsections. The sum of the light intensity coming from the zero and 90 degree subsections and the sum of the light intensity coming from the 45 and 135 degree subsections are each representative of the total amount of reflected light.

If the light reflected through the four subsections is completely depolarized by ice or snow, the two computed differences, $S_1$ and $S_2$, are small compared to the total energy observed. If the light reflected through the four subsections remains polarized due to the lack of a polarization altering substance, at least one of the computed differences will be large compared to the total energy observed. Without ice or snow present, the Stokes coefficients combine such that the square root of the sum of the squares of coefficients $S_1$ and $S_2$ divided by $S_0$ approximates unity, where $S_1$ is the difference in intensities observed between the zero degree axis subsection and the 90 degree axis subsection, $S_2$ is the difference in intensities observed between the 45 degree axis subsection and the 135 degree axis subsection, and $S_0$ is either the sum of the intensities of the zero and 90 degree subsections or the sum of the intensities of the 45 and 135 degree subsections. In other words, the reflected light is approximately 100% polarized.

Figure 11B:
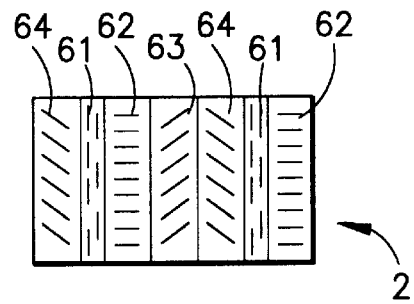
FIG. 11b shows an alternative embodiment of a polarizing filter patch in which one subsection is differentiated from the others.

Referring to FIG. 11b, subsection 61, which has its polarizing axes aligned at zero degrees, is differentiated from subsections 62, 63, and 64 by being narrower. Assuming that the subsections are always in a specified order, this differentiation allows a viewer to identify each subsection. Other methods of differentiation, such as differing geometrical shapes and designs, are within the contemplation of this invention. If the area of subsection 61 differs from the area of subsections 62, 63, and 64, one skilled in the art can adjust for different areas when computing the coefficients.

Figure 11C:
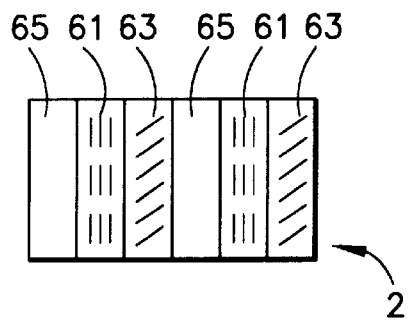
FIG. 11c shows an alternative embodiment of a polarizing filter patch using an unpolarized subsection and two linear polarized subsections.

Referring to FIG. 11c, an alternative embodiment uses three subsections. An unpolarized subsection 65 is used in addition to a zero degree subsection 61 and a 45 degree subsection 63. For scaling purposes, it is preferable that unpolarized subsection 65 of filter patch 2 attenuate light passing through it by the same amount as subsections 61 or 63. With this configuration, the viewing linear polarizer is position independent. When viewed through the viewing linear polarizer, the intensity of the light viewed from the unpolarized portion is representative of $S_0$, the total intensity. Since the unpolarized light loses half its intensity in passing through the viewing linear polarizer, the intensity of the light viewed from the unpolarized portion is at half the amplitude it would be if viewed through an unpolarized filter. The equivalent to $S_1$ is determined by subtracting the viewed amplitude of the zero degree portion from the viewed amplitude of the unpolarized portion. The equivalent to $S_2$ is determined by subtracting the viewed amplitude of the 45 degree portion from the viewed amplitude of the unpolarized portion.

If no ice is present, the square root of the sum of the squares of the $S_1$ and $S_2$ equivalents, divided by the $S_0$ equivalent (the viewed amplitude of the unpolarized portion), approximates unity, i.e., 100% polarization. If there is complete polarization due to a substance such as ice or snow, the viewed amplitude of all the portions will be the same. The $S_1$ and $S_2$ equivalents are therefore zero, and the square root of the sum of the squares of the $S_1$ and $S_2$ equivalents, divided by the $S_0$ equivalent, equals zero, or 0% polarization.

Figure 7:
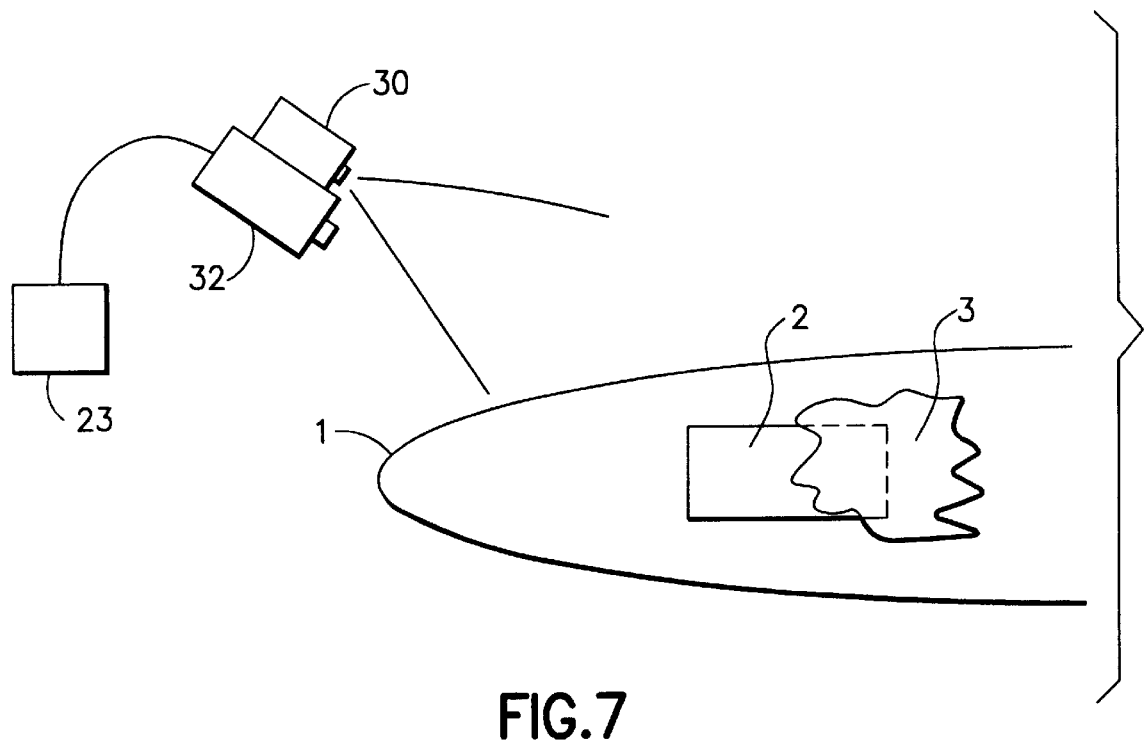
FIG. 7 shows an embodiment of the present invention using an active system.

Referring to FIG. 7, using a polarizing filter patch 2 on an aircraft wing 1 is also advantageous in an active mode. An active mode uses a polarized or unpolarized laser, strobe, or other light source, either in a floodlight illumination mode or in a point by point illumination scanning mode. A scene illuminated with a floodlight, or a transmitter 30, is recorded with a CCD (charge coupled device) camera 32 or other type of solid state camera. Images are sent to a computer 23 via a frame snatcher (not shown) for analysis. The scene lit by point by point scanning is normally evaluated on a point by point basis using a single detector element imaged by receiving optics arranged coaxially with the illumination source. Arrangements of both types are known in the art. Given a fixed advantageous position for both viewing and illuminating, if the laser or other source used to illuminate the patch covered wing is polarized, it must have its polarization axis approximately aligned with that of filter patch 2 or else no energy penetrates to the reflecting surface underneath. Regardless of whether the reflecting surface is metal or painted matte, a significant portion of the received energy is reflected (assuming a high reflectivity surface). All of the reflected light is polarized on the way out due to filter patch 2. Observation with isolating (blocking) and non-isolating (non blocking) filters discloses a significant difference between ice-free portions and portions that are covered with clear ice or snow, in exactly the same way as previously discussed.

The energy returned from the wing surface at the filter patch in the non-isolating mode (aligned polarizers) is always very large compared to that observed in the isolating mode (crossed polarizers) except for two cases. First, in areas where there is ice over the polarizing material, the light is significantly depolarized on the way out. The return is seen as significantly brighter than is usual for the ice-free case in the isolating mode. When ice, thin snow, or slush is present over the patch, the light is also attenuated on the way in to the reflective surface due to poor transparency. This loss is equal for both isolating and non-isolating modes, so it does not affect the ratio between the two.

Second, when the wing surface at the filter patch is covered with snow or slush, much of the light is immediately depolarized and reflected back towards the viewing apparatus without passing through the filter patch. This causes the energy seen in the isolating mode to be quite large, almost as large as that seen in the non-isolating mode. Thus, when the filter patch is snow covered, it provides a clear indication that a "clean wing" (as indicated by a high ratio of non-isolating to isolating mode energy received) is not present.

The utility of using a polarizing material over the wing surface is that the returned light must pass through the polarizer on the way out from the wing surface. A "clean wing" surface provides a highly polarized light return even if the surface is viewed at an extremely oblique angle. When bare metal is viewed obliquely, the polarizing ratio becomes much smaller because the return light is less specular in nature and thereby less well polarized. According to the present invention, if the underlying surface is painted matte white, more light returns to the viewer so that the surface maintains a constant brightness regardless of viewing angle. This painting could not be done in previous methods (except where the paint is metallic) because the paint destroys the specularity of the material and so destroys its polarization maintaining characteristics. Although the matte white paint underlying the polarizing filter patch destroys polarization, the light is repolarized while passing through the polarizing patch on the return trip.

The present invention enables detecting a polarization altering substance on other than specular surfaces. Ice is easily detected on composite wings of advanced aircraft, for example, as well as on surfaces which have been specularly reduced to minimize a reflected radar signature.

It is also contemplated that the surface of the filter patch exposed to the environment be anti-reflection (AR) coated or otherwise treated to avoid the surface reflection typical of transparent materials due to the mismatch between the optical index of the material and the optical index of air. Typically, this reflection amounts to approximately 4% of the impinging light for a material having an optical index of 1.5. Surface reflection is of concern primarily when the external or ambient illumination source, the surface normal, and the receiver or viewer are in a configuration that produces a specular viewing relationship. Optionally, roughening or dimpling the surface of the filter patch diminishes the specular effect which otherwise superimposes an unwanted image of the illumination source on the scene viewed by the receiver.

Figure 11D:
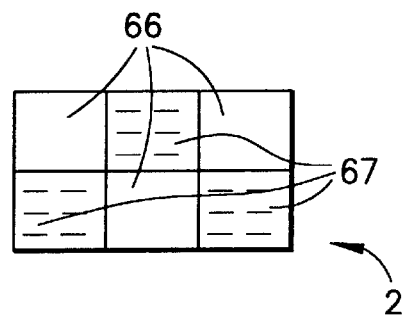
FIG. 11d shows an alternative embodiment of a polarizing filter patch using a pattern of polarized portions and unpolarized reflecting portions.

Referring to FIG. 11d, it is possible to view a circular polarizing filter patch or a linear polarizing filter patch from a known location, or orientation, with respect to the orientation of the filter patch. That is, a properly aligned blocking filter is used. In this event, the various stripes or patterns of differently aligned (linear) or contra-rotating (circular) polarizing filters are replaced with a reflective material, such as paint, on the upper surface of the filter patch or adjacent to it to provide either a brightness reference area or a pattern. Reflective portion 66 of filter patch 2 is shown in a checkerboard pattern with polarizing portion 67.

Other patterns are obvious to one skilled in the art as long as they provide enough contrast between the reflective portion and the polarizing portion. The sizes of the portions of the pattern are determined by the purpose for detecting the polarization altering substance, since if the substance is entirely within the unpolarized areas, it remains undetected.

When no ice or snow is present, filter patch 2 viewed through its viewing blocking polarizer appears dark with respect to the brightness reference area. When a depolarizing substance is present, the filter patch viewed through its viewing blocking polarizer appears brighter with respect to the brightness reference area. A reliable contrast or amplitude ratio is determined for an ice detection threshold. This threshold is used for future viewings.

Similarly, a covering of snow which covers both the reference portion and the filter patch will lower or eliminate the pattern contrast between the brightness reference area, or areas, and the polarized portions of the filter patch. Pattern locating or recognition algorithms are well known in the art of machine vision and use normalized correlation, vector correlation, hough transforms, or other standard techniques. Once the pattern is located, the various portions are isolated for the requisite amplitude, i.e., brightness, measurements. The human eye, viewing through a blocking polarizer, can be used for a rough determination of such pattern contrast, but does not substitute for the repeatability obtained using an imaging device such as a camera or other light measuring and recording instrument.

Figure 8:
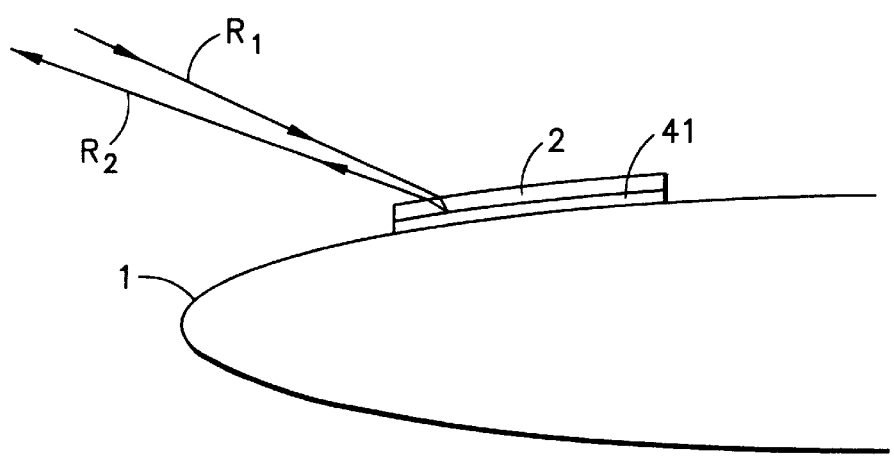
FIG. 8 shows an embodiment of the present invention combining the use of a light-emitting system with a retroreflective surface.

Referring to FIG. 8, in an active system using polarized light to detect ice by using a polarizing wing patch 2, it is also possible to further enhance the signal using a retroreflector 41 between aircraft wing 1 and polarizing surface patch 2. Conventional retroreflector materials are commercially available under the trademark Scotchlite, among others, in the form of rolls, sheets, tapes, and even paints. This material often consists of small spherical glass or plastic beads on a white paper or plastic surface. A transparent plastic layer covers the glass beads. As is well known, a transparent sphere returns light very strongly toward the light source. This is the effect seen in the blazing eyes of a cat illuminated at night by the headlights of a car. The rear surface of the retroreflective material is conventionally coated with an adhesive for affixing to a surface. When a colored retroreflective material is desired, a color filter layer is disposed over the front of the material. This is the method used to produce green and blue road signs and red stop signs. That is, the white background layer is covered by a transparent colored layer from which the appropriate portions have been cut. For example, a colored layer for a stop sign includes the word "STOP" cut out near its center so that this word is clearly visible both day and night.

With the transmitting and viewing apparatus located collinearly or in close proximity, retroreflector 41 causes almost all of the transmitted light $R_1$ to be returned to the viewing optics as reflected light $R_2$. This improves the good signal to noise (desired signal above background light, etc.) ratio, even when using a relatively low power illumination source, or alternatively, using a relatively small collection aperture for the viewing apparatus. Besides the tape described above, retroreflector 41 may be in the form of an adhesive layer onto which the spherical transparent beads are deposited. This latter form is most often seen in highway lane and edge striping. Such retroreflectors are well known and commercially available for various safety uses from 3M and other companies.

As an alternative, for small surfaces, the polarizing material on the wing may be backlit with a light source (not shown), preferably pulsed to allow separation from ambient light. The video camera 4 shown in FIG. 1 is then used to detect ice in the same manner as for frontal illumination. The backlit illumination is introduced via fiber optics or other means. Laser diodes can be used to generate high-power narrow-pulse light beams that are easily visible above ambient light including sunlight. In low-light applications, an electroluminescent panel may be used as a substrate for retroreflector 41.

It will be recognized by one skilled in the art that the above disclosure is equally applicable to forms of electromagnetic energy that exhibit polarization other than light.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. An apparatus for detecting a polarization altering substance on a surface, comprising:
    a first polarizing filter on said surface;
    said first polarizing filter including alternating regions having different axes of polarization;
    means for detecting, through a second polarizing filter, ambient polarized light and ambient nonpolarized light reflected from said surface; and
    means for calculating a parameter responsive to said means for detecting, said parameter being effective to indicate a presence of a polarization altering substance on said surface.

2. An apparatus for detecting a polarization altering substance according to claim 1, wherein:
    said alternating regions are linearly polarized; and
    said second polarizing filter is linearly polarized.

3. An apparatus for detecting a polarization altering substance according to claim 1, wherein:
    said alternating regions are circularly polarized; and
    said second polarizing filter is circularly polarized.

4. An apparatus for detecting a polarization altering substance according to claim 1, wherein said means for detecting includes at least one of a camera, polarized glasses, a polarizer, a photoelastic modulator, a rotating retarder plate a time varying retarder, and a charged coupled device.

5. An apparatus for detecting a polarization altering substance on a surface, comprising:
    a first polarizing filter on said surface;
    means for detecting ambient polarized light and ambient nonpolarized light reflected from said surface separately through blocking and unblocking filters;
    means for calculating a parameter responsive to said means for detecting, said parameter being effective to indicate a presence of a polarization altering substance on said surface.

6. An apparatus for detecting a polarization altering substance according to claim 5, wherein:
    said means for detecting includes first viewing means for viewing said surface through said blocking filter and includes second viewing means for viewing said surface through said unblocking filter; and
    said means for calculating includes means for comparing a response to said first viewing means and said second viewing means to determine a presence of said polarization altering substance.

7. An apparatus for detecting a polarization altering substance according to claim 5, wherein said first polarizing filter includes alternating regions having different axes of polarization.

8. An apparatus for detecting a polarization altering substance according to claim 5, wherein said first polarizing filter includes alternating regions having respective axes of polarization of zero degrees, 45 degrees, 90 degrees, and 135 degrees.

9. An apparatus according to claim 8, wherein:
    said alternating regions are in a specified sequence; and
    means for distinguishing at least one of said alternating regions.

10. An apparatus for detecting a polarization altering substance according to claim 5, wherein said means for detecting includes at least one of a camera, polarized glasses, a polarizer, a photoelastic modulator, a rotating retarder plate, a time varying retarder and a charged coupled device.

11. An apparatus for detecting a polarization altering substance on a surface, comprising:
    a filter on said surface;
    said filter including an unpolarized portion and two linear polarized portions;
    said two linear polarized portions having polarization axes 45 degrees apart;
    means for detecting, through a second polarizing filter, ambient polarized light and ambient nonpolarized light reflected from said surface; and
    means for calculating a parameter responsive to said means for detecting, said parameter being effective to indicate a presence of a polarization altering substance on said surface.

12. An apparatus for detecting a polarization altering substance on a surface, comprising:
    a filter on said surface;
    said filter including at least one unpolarized portion and at least one polarized portion;
    means for providing a brightness reference in said at least one unpolarized portion;
    means for detecting, through an aligned blocking polarized filter, ambient polarized light and ambient nonpolarized light reflected from said surface; and
    means for calculating a parameter responsive to said means for detecting, said parameter being effective to indicate a presence of a polarization altering substance on said surface.

13. An apparatus for detecting a polarization altering substance on a surface, comprising:
    a first polarizing filter on said surface;
    a filter strip including a series of specified filters;
    means for measuring a series of views through said filter strip, one view through each specified filter, to obtain a series of measurements;
    means for determining a set of Stokes coefficients from said series of measurements;
    means for determining, from said set of Stokes coefficients, a ratio of polarized ambient light returned from said surface compared to unpolarized ambient light returned from said surface, whereby a presence of a polarization altering substance on said surface may be detected.

14. An apparatus for detecting a polarization altering substance according to claim 13, wherein said first polarizing filter includes alternating regions having different axes of polarization.

15. An apparatus for detecting a polarization altering substance according to claim 13, wherein said first polarizing filter includes alternating regions having orthogonal polarizing properties.

16. An apparatus for detecting a polarization altering substance according to claim 13, wherein said filter strip includes:

a second polarizing filter;

a third polarizing filter;

a fourth polarizing filter;

a fifth polarizing filter;

said second and third polarizing filters having angles of polarization at 90 degrees from each other;

said fourth and fifth polarizing filters having angles of polarization at 90 degrees from each other;

an unpolarized filter;

a clockwise polarized filter; and a counterclockwise polarized filter.

17. An apparatus for detecting a polarization altering substance according to claim 16, wherein:

said second polarizing filter has an angle of polarization of 0 degrees;

said third polarizing filter has an angle of polarization of 90 degrees;

said fourth polarizing filter has an angle of polarization of 45 degrees; and said fifth polarizing filter has an angle of polarization of 135 degrees.

18. An apparatus for detecting a polarization altering substance on a surface, comprising:

a polarizing filter on said surface;

means for determining at least two Stokes parameters;

means for measuring, from said set of Stokes parameters, a ratio of polarized ambient light returned from said surface compared to unpolarized ambient light returned from said surface, whereby a presence of a polarization altering substance on said surface may be detected.

19. An apparatus according to claim 18, wherein said means for determining at least two Stokes coefficients includes a photoelastic modulator based polarimeter.

20. An apparatus according to claim 18, wherein said means for determining at least two Stokes coefficients includes a rotating retarder plate.

21. An apparatus according to claim 18, wherein said means for determining at least two Stokes coefficients includes a rotating polarizer.

22. An apparatus according to claim 18, wherein said means for determining at least two Stokes coefficients includes at least one time varying retarder element.

\* \* \* \* \*